United States Patent
Fukui et al.

(10) Patent No.: US 11,442,070 B2
(45) Date of Patent: Sep. 13, 2022

(54) BLOOD ANALYSIS METHOD AND BLOOD TEST KIT

(71) Applicant: FUJIFILM Corporation, Tokyo (JP)

(72) Inventors: Kota Fukui, Kanagawa (JP); Shinya Sugimoto, Tokyo (JP); Isao Yonekubo, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 20 days.

(21) Appl. No.: 16/454,064

(22) Filed: Jun. 27, 2019

(65) Prior Publication Data

US 2019/0317112 A1   Oct. 17, 2019

Related U.S. Application Data

(63) Continuation of application No. PCT/JP2017/047202, filed on Dec. 28, 2017.

(30) Foreign Application Priority Data

Dec. 28, 2016  (JP) .............................. JP2016-255675

(51) Int. Cl.
*G01N 33/72* (2006.01)
*G01N 1/38* (2006.01)
(Continued)

(52) U.S. Cl.
CPC ............. *G01N 33/721* (2013.01); *G01N 1/38* (2013.01); *G01N 33/491* (2013.01)

(58) Field of Classification Search
CPC ...... G01N 33/721; G01N 1/38; G01N 33/491; G01N 33/96; G01N 33/48
See application file for complete search history.

(56) References Cited

U.S. PATENT DOCUMENTS 6,268,167 B1   7/2001 Wild et al.
8,802,025 B2   8/2014 Narikawa et al.
(Continued)

FOREIGN PATENT DOCUMENTS

CN   101743469   6/2010
CN   102297801   12/2011
(Continued)

OTHER PUBLICATIONS

"Office Action of Japan Counterpart Application", dated Apr. 7, 2020, with English translation thereof, p. 1-p. 6.
(Continued)

*Primary Examiner* — Tracy Vivlemore
*Assistant Examiner* — Nam P Nguyen
(74) *Attorney, Agent, or Firm* — JCIPRNET (57) ABSTRACT

An object of the present invention is to provide a blood analysis method and a blood test kit, which are capable of performing measurement of a plurality of target components to be analyzed with high accuracies in a case where hemolysis occurs in a case of measuring an amount of target components to be analyzed in a small volume of a blood sample. According to the present invention, provided is a blood analysis method for measuring a concentration of a target component to be analyzed, the blood analysis method including: a step of diluting a collected blood sample with a diluent solution, a step of determining a dilution factor by using a normal value of a normal component which is homeostatically present in blood, a step of analyzing the concentration of the target component to be analyzed in the blood sample, measuring an amount of hemolysis in the blood sample, correcting the dilution factor according to the measured amount of hemolysis, and analyzing the concentration of the target component to be analyzed using the corrected dilution factor.

7 Claims, 5 Drawing Sheets

(51) Int. Cl.
*G01N 33/49* (2006.01)
*G01N 33/48* (2006.01)
*G01N 33/96* (2006.01)

(56) References Cited

U.S. PATENT DOCUMENTS

| | | |
|---|---|---|
| 2001/0055784 A1 | 12/2001 | Noda et al. |
| 2002/0153316 A1 | 10/2002 | Nanba et al. |
| 2003/0175167 A1 | 9/2003 | Takanori et al. |
| 2004/0141888 A1 | 7/2004 | Nanba et al. |
| 2007/0054404 A1 | 3/2007 | Huo et al. |
| 2012/0015388 A1 | 1/2012 | Takagi et al. |
| 2015/0225768 A1 | 8/2015 | Yawata et al. |
| 2017/0205433 A1* | 7/2017 | Osawa ........... C12Y 302/01023 |
| 2020/0319215 A1* | 10/2020 | Osawa ................... G01N 33/49 |

FOREIGN PATENT DOCUMENTS

| | | |
|---|---|---|
| EP | 0268025 | 5/1988 |
| EP | 0574267 | 12/1993 |
| EP | 2695573 | 2/2014 |
| EP | 2700358 | 11/2014 |
| EP | 3321675 | 5/2018 |
| EP | 3321676 | 5/2018 |
| EP | 3321677 | 5/2018 |
| EP | 3321678 | 5/2018 |
| JP | S59168371 | 9/1984 |
| JP | S6350743 | 3/1988 |
| JP | H08101191 | 4/1996 |
| JP | 2001074748 | 3/2001 |
| JP | 2001221794 | 8/2001 |
| JP | 2001330603 | 11/2001 |
| JP | 2003161729 | 6/2003 |
| JP | 2003270239 | 9/2003 |
| JP | 3597827 | 12/2004 |
| JP | 3698696 | 9/2005 |
| JP | 2009109196 | 5/2009 |
| JP | 2009122082 | 6/2009 |
| JP | 2014062785 | 4/2014 |
| JP | 5906604 | 4/2016 |
| JP | 2016118565 | 6/2016 |
| WO | 2013147200 | 10/2013 |
| WO | WO-2016013388 A1 * | 1/2016 |

OTHER PUBLICATIONS

Susumu Osawa, et al., "Delivery Method of the Test Results and the Clinical Laboratory Technology and Offer of the Clinical Laboratory Technology to be Possible at Home," Japanese Journal of Clinical Laboratory Automation, vol. 41, 2016, pp. 154-160.
"Search Report of Europe Counterpart Application", dated Sep. 25, 2019, p. 1-p. 6.
Office Action of China Counterpart Application, with English translation thereof, dated Dec. 17, 2019, pp. 1-9.
Osawa, Susumu et al., "Revolution of medical services at home using a small amount of blood collected from the fingertip", Journal of Clinical Laboratory Medicine,vol. 59, No. 5,May 15, 2015, pp. 1-9.
Osawa, Susumu et al., "Development of an assay for measuring biochemical parameters in 65-µL fingertip blood samples collected at home", 68th AACC Annual Scientific Meeting Abstracts, Aug. 3, 2016, pp. 1-1.
"International Search Report (Form PCT/ISA/210) of PCT/JP2017/047202," dated Apr. 3, 2018, with English translation thereof, pp. 1-4.
"Written Opinion of the International Searching Authority (Form PCT/ISA/237) of PCT/JP2017/047202," dated Apr. 3, 2018, with English translation thereof, pp. 1-9.
Office Action of European Counterpart Application, dated Mar. 21, 2022, pp. 1-5.

* cited by examiner

BLOOD ANALYSIS METHOD AND BLOOD TEST KIT

CROSS-REFERENCE TO RELATED APPLICATIONS

This application is a Continuation of PCT International Application No. PCT/JP2017/047202 filed on Dec. 28, 2017, which claims priority under 35 U.S.C § 119(a) to Japanese Patent Application No. 2016-255675 filed on Dec. 28, 2016. Each of the above application(s) is hereby expressly incorporated by reference, in its entirety, into the present application.

BACKGROUND OF THE INVENTION

1. Field of the Invention

The present invention relates to a blood analysis method and a blood test kit, which are for measuring a concentration of a target component to be analyzed in a blood sample.

2. Description of the Related Art

As blood collection, in general, there are general blood collection in which a qualified person such as a doctor collects blood from the vein using a syringe, and self-blood collection in which a subject to be tested pricks his finger and the like using a blood collection needle so as to collect blood.

The blood collected by the general blood collection is transported to a medical institution or a test institution in a state of being sealed in a blood collection container, and tests are performed therein. In a case where the blood is transported without separating blood cells and blood plasma, tests are performed after a medical institution or a test institution separates the blood into blood cells and blood plasma with a centrifuge. In addition, in the self-blood collection which is performed by a subject to be tested, the collected blood is separated into blood cells and blood plasma by a separation membrane, the blood is transported to a test lab in this separated state, and then tests are performed therein.

JP2003-161729A discloses a method for testing a blood sample collected by self-blood collection. JP2003-161729A specifically discloses a method for quantitatively determining a component to be quantitatively determined in a biological specimen, the method including 1) step of preparing a specimen for quantitation composed of a biological specimen with an unknown volume which contains a component to be quantitatively determined, which is collected without quantitatively determining a volume thereof, and an aqueous solution with a certain volume which contains a certain amount of an indicator substance; 2) step of obtaining a dilution factor (a) of the biological specimen from a concentration ($C_1$) of the indicator substance in the aqueous solution with a certain volume which contains a certain amount of the indicator substance, and a concentration ($C_2$) of the indicator substance in the specimen for quantitation; 3) step of obtaining a concentration (Y) of the component to be quantitatively determined in the specimen for quantitation; and 4) step of determining the component to be quantitatively determined in the biological specimen from the dilution factor (a) of the biological specimen obtained in 2), and the concentration (Y) of the substance to be quantitatively determined in the specimen for quantitation obtained in 3).

JP2001-330603A discloses a quantitative analysis method in which an amount of a target component to be analyzed in a sample is measured; an amount of a normal component other than the target component to be analyzed, which is originally and homeostatically present in the sample, is measured; a volume of the sample is determined from the amount of this normal component and a known concentration of the normal component in the sample; and a concentration of the target component to be analyzed in the sample is determined from the volume of this sample and the amount of the target component to be analyzed.

In addition, JP2009-122082A discloses that, using an instrument for blood dilution and quantitation, a small volume of blood is collected from a human or an animal, and after dilution or without dilution, a certain volume thereof is supplied to another instrument or container or is directly supplied to a reagent. Furthermore, JP2009-109196A discloses a method for quantitatively determining a concentration of a component to be quantitatively determined in a biological specimen by utilizing an absorbance of an indicator substance in an aqueous solution for dilution.

JP2016-118565A discloses a quantitative analysis method for measuring a concentration of a target component to be analyzed in a sample, in which an amount of the target component to be analyzed in the sample is measured, an amount of a normal component which is other than the target component to be analyzed and which is originally and homeostatically present in the sample is measured, a volume of the sample is determined from the amount of this normal component and a known concentration of the normal component in the sample, and the concentration of the target component to be analyzed in the sample is determined from the volume of this sample and the amount of the target component to be analyzed; and discloses a method for analyzing of a diluted biological specimen in an external standard method.

JP1996-101191A (JP-H08-101191A) discloses a method for analyzing a medical sample while avoiding measurement errors due to hemolysis, the method including, after the sample is subjected to a preliminary reaction, measuring a degree of hemolysis of the sample in the reaction prior to actual measurement of components present in the sample by a photometry; and correcting measurement values thus obtained of the test components using numerical values determined by correlation between the degree of hemolysis and measurement error contribution by interference components.

SUMMARY OF THE INVENTION

In the method disclosed in JP2003-161729A, it is required that a ratio of a diluent solution to a blood sample volume be set high in a case of a small volume of a blood sample. However, in this case, a change rate in a volume of a diluent solution before and after diluting the blood sample becomes very small, and thus a change rate in a concentration of an internal standard substance becomes small. Therefore, there is a problem of a decrease in level of repeatability and reproducibility with respect to measurement values.

JP2001-330603A discloses that about 100 µL of whole blood of a healthy subject is added dropwise to a porous membrane, blood cells are separated to develop blood serum, and thereafter, a solution obtained by adding 150 µL of a physiologically isotonic phosphate-buffered saline (PBS, pH of 7.4) thereto is centrifuged, and a supernatant thus obtained is analyzed as an analytical specimen, but does not disclose collection of blood of less than 100 µL.

In the method of JP2009-122082A, 10 μL of a blood volume is precisely collected with a micropipette so as to be analyzed, but in a case where the blood is collected by a patient who lacks experience in blood collection, it is difficult to precisely collect a certain volume thereof, resulting in errors in measurement values in a case where tests are performed with collected blood volumes including errors.

The measurement method disclosed in JP2009-109196A is the measurement with a dilution factor of about 10, but in a case where a dilution factor is further raised to sufficiently secure a volume of diluted blood, there is the same problem as in JP2003-161729A of a decrease in level of repeatability and reproducibility with respect to measurement values.

JP2016-118565A discloses that, in the method, a dilution factor of a blood specimen is calculated using an internal standard substance and an external standard substance. However, in a case where hemolysis of blood components occurs, concentrations of a normal component in blood cells and blood plasma become different from each other, and therefore the concentration of a normal component in blood plasma is affected by the concentration of a normal component in blood cells. For example, in a case of sodium ions, a concentration thereof in blood cells is lower than a concentration thereof in blood plasma, and in a case where hemolysis occurs, the concentration thereof is lowered. Therefore, in a case where a dilution factor is determined using sodium present in blood plasma as an external standard substance, extremely large errors are generated. As described above, in the description of JP2016-118565A, there is a concern that measurement accuracies of quantitative analysis is lowered in a case where hemolysis occurs.

Meanwhile, in order to alleviate pain of a patient or subject to be tested, there is need of a measurement method for measuring, with high accuracies, a plurality of target substances from a small volume of a blood sample. In this case, a method for measuring a plurality of target substances by diluting a small volume of blood to increase the volume thereof so as to be usable in measurement is performed. In this case, it is required to determine a dilution factor of a blood sample. JP1996-101191A (JP-H08-101191A) discloses a technique for correcting a target substance when hemolysis, which is the problem of JP2016-118565A, occurs. However, there is no description of correction of diluted blood, and no description regarding measurement of a plurality of target substances from a small volume of blood. Therefore, in a case of a small volume of a blood sample, there is a problem of analyzable target substances being limited.

As described above, even in a case where the method for correcting a target component by an amount detected of hemoglobin is applied to JP2016-118565A in order to solve the problem of JP2016-118565A, a problem is not solved in which, in a case where hemolysis occurs in a sample, concentrations of a normal component in blood cells and blood plasma become different from each other, and therefore the concentration of a normal component in blood plasma is affected by the concentration of a normal component in blood cells. Therefore, it is not possible to analyze a plurality of target substances from a small volume of blood with high measurement accuracies.

An object of the present invention is to provide a blood analysis method and a blood test kit, which are for measuring a concentration of a target component to be analyzed in a blood sample, the blood analysis method and the blood test kit being capable of performing measurement of a plurality of target components to be analyzed with high accuracies in a case where hemolysis occurs in a case of measuring an amount of target components to be analyzed in a small volume of a blood sample as described above.

As a result of intensive studies to achieve the above-described object, the inventors of the present invention have found that measurement of a plurality of target components to be analyzed can be performed with high accuracies by measuring an amount of hemolysis in a blood sample and correcting a dilution factor according to the measured amount of hemolysis, in a blood analysis method for measuring a concentration of a target component to be analyzed, the method including diluting collected blood sample with a diluent solution, determining a dilution factor by using a normal value of a normal component which is homeostatically present in blood, and analyzing the concentration of the target component to be analyzed in the blood sample; and therefore have completed the present invention. That is, according to the present invention, the following inventions are provided.

(1) A blood analysis method for measuring a concentration of a target component to be analyzed, the blood analysis method comprising:
a step of diluting a collected blood sample with a diluent solution;
a step of determining a dilution factor by using a normal value of a normal component which is homeostatically present in blood; and
a step of analyzing the concentration of the target component to be analyzed in the blood sample,
in which the method performs
measuring an amount of hemolysis in the blood sample,
correcting the dilution factor according to the measured amount of hemolysis, and
analyzing the concentration of the target component to be analyzed using the corrected dilution factor.

(2) The blood analysis method according to (1), which is performed by using a blood test kit,
in which the blood test kit includes
the diluent solution for diluting the blood sample,
separating means for recovering a blood plasma component from the diluted blood sample, and
a container for storing the blood plasma component recovered from the diluted blood sample.

(3) The blood analysis method according to (2), in which the diluent solution contains a normal component not present in blood, and the blood test kit is for analyzing the concentration of the target component to be analyzed in the blood sample using the normal component not present in blood.

(4) The blood analysis method according to (2) or (3), in which the blood plasma component is recovered from the diluted blood sample by using the blood test kit, a dilution factor of the diluted blood sample is determined using the normal component which is homeostatically present in the recovered blood plasma component, and the concentration of the target component to be analyzed in the blood sample is analyzed.

(5) The blood analysis method according to any one of (2) to (4), in which the diluent solution contains a normal component not present in blood, and the blood test kit determines a dilution factor of the diluted blood sample using the normal component not present in blood, and analyzes the concentration of the target component to be analyzed in the blood sample.

(6) The blood analysis method according to any one of (1) to (5), in which the normal component homeostatically present in blood is at least one substance selected from sodium ions, chloride ions, potassium ions, magnesium ions, calcium ions, total proteins, or albumins.

(7) A blood test kit which is used in the blood analysis method according to any one of (1) to (6), the blood test kit comprising:

a diluent solution for diluting a blood sample;

separating means for recovering a blood plasma component from the diluted blood sample; and a container for storing the blood plasma component recovered from the diluted blood sample.

According to a blood analysis method and a blood test kit of the present invention, highly accurate analysis can be performed even in a case where a blood sample is hemolyzed.

DESCRIPTION OF THE PREFERRED EMBODIMENTS

Hereinafter, the present invention will be described in detail. A range indicated by X to Y includes values of an upper limit X and a lower limit Y. A normal component which is homeostatically present in blood may be referred to as an external standard substance or an external standard. In addition, a normal component which is not present in blood may be referred to as an internal standard substance or an internal standard.

An object of the present invention is to provide a blood analysis method for analyzing a concentration of a target component by diluting a small volume of a blood sample with a buffer solution, the method capable of obtaining a dilution factor with accuracies not described in the related art in a case where analysis of a target component is performed using an external standard homeostatically present in blood. A solution for achieving the above-described object is to enable analysis of a concentration of a target component to be analyzed with high accuracies by measuring an amount of hemolysis in a blood sample and correcting a dilution factor according to the measured amount of hemolysis.

According to the present invention, it is possible to realize a blood measurement method and a blood analysis kit, which enable accurate measurement of a target substance, in which error factors of a dilution factor due to hemolysis caused by a separation rate and the like have been removed in a case where a patient himself collects blood and filters the collected blood with a separation membrane, in a measurement method for measuring a target component to be analyzed in blood.

The present invention relates to a blood analysis method for measuring a concentration of a target component to be analyzed, the blood analysis method includes:

a step of diluting a collected blood sample with a diluent solution;

a step of determining a dilution factor by using a normal value of a normal component which is homeostatically present in blood, and a step of analyzing the concentration of the target component to be analyzed in the blood sample, in which the method performs measuring an amount of hemolysis in the blood sample, correcting the dilution factor according to the measured amount of hemolysis, and analyzing the concentration of the target component to be analyzed using the corrected dilution factor.

Analyzing a concentration of the target component in the blood sample includes determining a concentration of the target component (that is, quantitatively determining the target component), determining whether a concentration of the target component is equal to or higher than a predetermined reference value or is equal to or lower than a predetermined reference value, and the like. An aspect of the analysis is not particularly limited.

(Hemolysis)

In the present invention, hemolysis refers to elution of components in blood cells into blood plasma due to the destruction of blood cell membranes due to external energy such as vibration or shear. In a case where elution occurs due to a difference between concentrations in blood cells and blood plasma, a concentration of homeostatic components in blood plasma changes, and therefore a correct dilution factor cannot be calculated. The present invention provides a method for correcting these problems. A degree of hemolysis can be obtained by calculating a concentration (mg/dL) of hemoglobin in blood plasma. In the present invention, this concentration value (mg/dL) of hemoglobin is defined as a degree of hemolysis.

In blood plasma, sodium ions account for the majority of cations, whereas in blood cells, potassium ions account for the majority of cations, and a concentration of sodium ions in blood cells is relatively low as compared to a concentration of sodium ions in blood plasma. In addition, it is known that an amount of total protein present in blood cells is different from an amount of total protein present in blood plasma. In a case where hemolysis occurs, a concentration of sodium ions in blood plasma decreases, and a concentration of total protein increases. Accordingly, a case where these sodium ions or total proteins are used as standard substances for measuring a dilution factor, leads to a result in which calculated dilution factors vary due to the occurrence of hemolysis. Therefore, there is a concern that the measurement accuracies may be lowered. In the present invention, a concentration of hemoglobin eluted into blood plasma due to hemolysis is measured; an amount of hemolysis is determined as a degree of hemolysis; using this degree of hemolysis, a concentration of standard substances such as sodium ions or total proteins in a mixture of a diluent solution and blood plasma is corrected; a dilution factor is corrected using the corrected concentration of standard substances; and thus it becomes possible to obtain, with high accuracies, a concentration of a target substance to be measured in blood plasma using the corrected dilution factor.

[Method for Collecting Blood Sample and Collected Volume]

In the present invention, a blood sample is collected to analyze a target component in a blood sample. The collection of blood in the blood analysis method of the embodiment of the present invention may be performed by a subject to be tested himself or may be performed by a qualified person such as a doctor.

In a preferred embodiment, a patient himself injures a fingertip and the like using a blade-attached instrument such as a lancet and then collects the blood flowing out of the skin. It is preferable that the blood be collected in a manner of decreased invasiveness so as to alleviate the burden on a patient. It is more preferable to be able to collect the blood painlessly or with extremely little pain when collecting the blood, and in this case, it is desired that a depth and a size of the wound be small, and a volume of blood that can be collected becomes very small. Accordingly, a volume of a sample collected by the blood test kit of the embodiment of the present invention (that is, a volume of blood collected) is preferably 100 μL or less, more preferably 70 μL or less, and even more preferably 50 μL or less.

[Normal Component Homeostatically Present in Blood]

As described above, it is required to precisely analyze a concentration of a target component present in plasma of blood before dilution with respect to a target component after dilution of diluted blood plasma, in which a dilution factor of blood plasma components is large. In a case where a concentration of a target component is obtained from a rate of change in concentrations of a substance present in a diluent solution in advance as a standard substance, the rate of change in concentrations is extremely small, and therefore there is an adverse effect in which measurement errors are likely to occur, and reproducibility of measurement deteriorates. Accordingly, the blood analysis method of the embodiment of the present invention is performed by a blood analysis method for analyzing a concentration of a target component in a blood sample using a normal component which is homeostatically present in blood.

"Use" of a normal component means determination of a dilution factor for analyzing a concentration of a target component based on a normal value (homeostatic value) of the normal component. Accordingly, analyzing a concentration of a target component in a blood sample using a normal component homeostatically present in blood also means that analyzing of a concentration of a target component by determining a dilution factor based on a homeostatic value (a normal value) of the normal component homeostatically present in blood.

Examples of normal components homeostatically present in blood include sodium ions, chloride ions, potassium ions, magnesium ions, calcium ions, total proteins, albumins, and the like. As a concentration of these normal components contained in blood serum and blood plasma of a blood sample, a concentration of sodium ions is 134 to 146 mmol/L (average value: 142 mmol/L), a concentration of chloride ions is 97 to 107 mmol/L (average value: 102 mmol/L), a concentration of potassium ions is 3.2 to 4.8 mmol/L (average value: 4.0 mmol/L), a concentration of magnesium ions is 0.75 to 1.0 mmol/L (average value: 0.9 mmol/L), a concentration of calcium ions is 4.2 to 5.1 mmol/L (average value: 4.65 mmol/L), a concentration of total proteins is 6.7 to 8.3 g/100 mL (average value: 7.5 g/100 mL), and a concentration of albumins is 4.1 to 5.1 g/100 mL (average value: 4.6 g/100 mL). In the present invention, it is possible to measure a target component with high accuracies even in a case where a volume of blood collected is extremely small for relieving pain of a patient. In a case where a volume of blood collected is small, it is necessary to measure a concentration of a "normal component which is homeostatically present in blood" and is present in a diluent solution with high accuracies. As a dilution factor becomes large, a concentration of a component, which is originally present in the blood, in the diluent solution decreases, and depending on dilution factors, measurement errors may be included at the time of measurement of the concentration. Accordingly, it is preferable to measure a normal component present at a high concentration in a small volume of the blood in order to detect the normal component with sufficiently high accuracies when a small volume of blood components is diluted by a large dilution factor. In the present invention, it is preferable to use sodium ions ($Na^+$) or chloride ions ($Cl^-$) which are present at a high concentration among the components homeostatically present in a blood sample. Furthermore, it is most preferable to measure sodium ions which are present in the blood at the largest amount among the above-mentioned normal components homeostatically present in blood. Regarding sodium ions, an average value represents a normal value (a median value within a reference range), and this value is 142 mmol/L accounting for 90 mole % or more of total cations in blood plasma.

An occupancy rate of blood plasma components in the blood of a subject to be tested is about 55% in terms of a volume ratio, but varies depending on changes in salt intake and the like of the subject to be tested. Therefore, in a case of analyzing a target component by the blood analysis method of the embodiment of the present invention, a dilution factor of blood plasma is determined by using a normal value of a normal component which is homeostatically present in blood plasma, and a concentration of a target component in the blood plasma of a blood sample is analyzed using the determined dilution factor. In this case, as a method for determining a dilution factor in a case where hemolysis of blood cells does not occur, or hemolysis occurs to the extent that hemolysis is negligible, it is possible to obtain a dilution factor by calculating a dilution factor ($Y/X$) of blood plasma components in a blood sample from a measurement value (concentration $X$) of an external standard substance (for example, sodium ions and the like) in a diluent solution of the blood plasma, and a known concentration value (concentration $Y$; in a case of sodium ions, 142 mmol/L) of the external standard substance (for example, sodium ions and the like) contained in blood plasma of the blood sample. Using this dilution factor, a measurement value (concentration $Z$) of a target component in a diluent solution of the blood plasma is measured, and by multiplying this measurement value by the dilution factor, it is possible to measure a concentration [$Z \times (Y/X)$] of a target component to be analyzed actually contained in the blood plasma of the blood sample.

However, in a case where a patient or subject to be tested separates blood cells from a diluent solution of blood, and the like, cases in which blood cells, particularly red blood cells are destructed, and blood cell components are eluted into blood, and thus influence of hemolysis is not negligible may occur. The present invention is a blood analysis method which enables analysis of a substance to be measured with high accuracies even in such a case. In the present invention, a relationship between a concentration of hemoglobin eluted into blood plasma due to hemolysis and a change in concentration of a normal component in the blood plasma is obtained in advance. From this relationship, a concentration of a standard substance in a blood plasma diluent solution, which affects calculation of dilution factors due to destruction of blood cells, is corrected. By correcting a dilution factor as described above, in the present invention, it is possible to analyze a target substance to be measured with high accuracies even in a case of hemolyzed blood.

External standard substances (for example, sodium ions and the like) in blood plasma change in a case where hemolysis occurs. In a case of sodium ions as an example, a relationship between a degree of hemolysis (a concentration (mg/dL) of hemoglobin) in a case where hemolysis occurs and an amount (mmol/L) X of change in concentration of sodium ions can be represented as follows.

Amount (X) of change in concentration=−0.0482× degree of hemolysis (concentration (mg/dL) of hemoglobin)   Equation 1:

The degree of hemolysis herein can be approximated by the following equation using a known concentration value (Y) of sodium ions, a measurement concentration value (W) of hemoglobin after blood plasma is diluted with a diluent solution, and a measurement concentration value (V) of sodium ions after blood plasma is diluted with a diluent solution. A unit of the known concentration value (Y) is mmol/L, and a unit of the measurement concentration value (V) of sodium ions is mmol/L. A unit of the measurement concentration value (W) of hemoglobin is mg/dL.

Degree of hemolysis≈measurement concentration value (W) of hemoglobin)×(known concentration value (Y)/measurement concentration value (V) of sodium ions)   Equation 2:

Using the amount (X) of change in concentration obtained from Equation 1 and Equation 2 according to this hemolysis, a concentration value (Z) of an external standard substance in blood plasma at the time of hemolysis can be represented by a sum of the known concentration value (Y) and the amount (X) of change in concentration. A unit of the concentration value (Z) at the time of hemolysis is mmol/L.

Concentration value (Z) at the time of hemolysis=known concentration value (Y)+ amount (X) of change in concentration   Equation 3:

Accordingly, from the measurement concentration value (V) of an external standard substance (for example, sodium ions and the like) in a mixed solution of blood plasma and a diluent solution, and the concentration value (Z) of the external standard substance at the time of hemolysis, it is possible to obtain a corrected dilution factor by the following equation. By multiplying the corrected dilution factor by a measurement concentration value of a target substance to be measured in a mixed solution of blood plasma and a diluent solution, it is possible to obtain a concentration of the target substance to be measured which is originally present in blood plasma with high accuracies.

Corrected dilution factor=concentration value (Z) at the time of hemolysis/measurement concentration value (V)   Equation 4:

A concentration of sodium ions and a concentration of chloride ions can be measured by, for example, a flame photometric method, a glass-electrode method, a titration method, an ion selective electrode method, an enzyme activity method, and the like.

In a case of measuring sodium ions, it is possible to use an enzymatic assay in which several µL of a specimen having a very low concentration of sodium ions, which has been diluted with a buffer solution, are measured by utilizing that the enzyme activity of the enzyme galactosidase is activated by sodium ions. This method can be applied to a biochemical/automated immunoassay analyzer, and is highly efficient and economical for not requiring another measuring instrument for measurement of sodium ions. In addition, in a case of using a concentration of total protein as a standard substance, examples of methods for measuring total proteins include known methods such as a biuret method, an ultraviolet absorption method, a Bradford method, a Lowry method, a bicinchoninic acid (BCA) method, and a fluorescence method. It is possible to appropriately select a method to be used depending on characteristics, sensitivity, a specimen amount, and the like of a measurement specimen.

In addition, in order to confirm whether correction by hemolysis is precisely performed or whether a method for diluting blood and recovering blood plasma is normally performed, it is preferable that an additional dilution factor be separately obtained from another normal component in blood plasma so as to check whether a value thereof matches with the dilution factor obtained above. The term "match" means, with respect to two measurement values (a, b), a ratio of a difference thereof to an average value thereof, that is, (a−b)/{(a+b)/2}×100 is 20% or smaller, is preferably 10% or smaller, and is more preferably 5% or smaller. Accordingly, it is possible to verify that analysis of a concentration of a target component in a blood sample has been normally performed. Examples of normal components homeostatically present in blood plasma, which are other than sodium ions and chloride ions, are preferably selected from total proteins or albumins, and are more preferably total proteins.

[Normal Component not Present in Blood]

As a preferred embodiment, it is possible to analyze a concentration of a target component in a blood sample using a normal component which is not present in blood but in a diluent solution, together with a normal component homeostatically present in blood, and to correct a dilution factor obtained from the normal component homeostatically present in blood. In addition, it is also possible to calculate a dilution factor with the normal component homeostatically present in blood.

It is possible to use the normal component not present in the blood by adding the normal component not present in the blood into a diluent solution (to be described later) of a kit such that a concentration thereof becomes a predetermined concentration. As the normal component not present in the blood, it is possible to use a substance which is not contained in the blood sample at all, or is contained therein in an ultra-small amount. As the normal component not present in the blood, it is preferable to use substances which do not interfere with measurement of a target component in a blood sample, substances which do not decompose under the action of biological enzymes in a blood sample, substances which are stable in a diluent solution, substances which do not pass through a blood cell membrane and thus are not contained in the blood cells, substances which are not absorbed into a storing container of a buffer solution, and substances which can be utilized by a detection system capable of measurement with high accuracies.

As the normal component not present in the blood, substances which are stable even in a case where the substances are stored for a long period of time in a state of being added into the diluent solution, are preferable. Examples of normal components not present in blood include glycerol 3-phosphate, Li, Rb, Cs, or Fr as alkali metal, and Sr, Ba, or Ra as alkaline earth metal. Among these, Li and glycerol 3-phosphate are preferable.

These normal components not present in blood develops color by adding, thereto, a second reagent at the time of measuring a concentration after blood dilution, and the concentration in the diluted blood can be obtained from a color optical density. For example, regarding measurement of lithium ions added into a diluent solution, a large number of specimens can be easily measured with a small amount of blood by using a chelate colorimetric method (a halogenated porphyrin chelating method: perfluoro-5,10,15,20-tetraphenyl-21H,23H-porphyrin) with an automatic biochemistry analyzer.

In this case, a dilution factor can be obtained by C1/(C1−C0) in a case where a concentration of a normal component which is in a diluent solution and which is not homeostatically present in blood is referred to as C1, and a concentration of a normal component which is homeostatically present in blood and which is in a mixed solution of a blood plasma component and a diluent solution is referred to as C0.

By using a blood test kit for analyzing a concentration of a target component in a blood sample using a normal component not present in blood (also referred to as an internal normal component), together with a normal component homeostatically present in blood (also referred to as an external normal component), that is, using two normal components in combination, it is possible to realize analysis having higher reliability.

In this case, it is preferable that a dilution factor of the components of a blood sample is calculated by any one of Formulas 5 to 8, and a concentration of the target component to be analyzed in the diluent solution is multiplied by the above dilution factor, and therefore a concentration of target component in the components of a blood sample is analyzed.

$$X=(A+C)/(B+D) \quad \text{Formula 5:}$$

$$X=\{(A^2+C^2)^{1/2}\}/\{(B^2+D^2)^{1/2}\} \quad \text{Formula 6:}$$

$$X=a\times(B+D)\pm b \quad \text{Formula 7:}$$

(where a and b are coefficients, and a standard curve represented by Formula 5 is prepared in advance by acquiring data of (B+D) and a dilution factor in advance)

$$X=A/B' \quad \text{Formula 8:}$$

(where B'=(A×D)/C)

In the above formulas, A, B, C, D, B', and X are defined as follows.

A: Measurement absorbance of the diluent solution containing an internal normal component B: Absorbance obtained by subtracting an absorbance of the diluted solution obtained by diluting the components of the blood sample from A C: Measured absorbance of the solution in which a concentration of sodium ions, as a homeostatic substance, is 142 mmol/L D: Absorbance of sodium ions in the diluted solution obtained by diluting the components of the blood sample B': A correction value of an absorbance of a normal component not present in blood in the diluted blood plasma obtained by a dilution factor calculated from the absorbance of the blood plasma sodium X: A dilution factor of blood plasma As another calculation method for a case of obtaining a dilution factor, an aspect in which a dilution factor is calculated by Formula 9 using a root-mean-square method, a concentration of a target component to be analyzed in a diluent solution is multiplied by the dilution factor calculated by Formula 9, and a concentration of a target component of components in a blood sample is analyzed, is preferable.

$$X=[\{(A/B)^2+(C/D)^2\}/2]^{1/2} \quad \text{Formula 9:}$$

A concentration of a target component of components in a blood sample can be calculated from a concentration of a target component in a diluent solution, based on the above-mentioned dilution factor.

[Diluent Solution]

In the blood analysis method of the embodiment of the present invention, a collected blood sample is diluted using a diluent solution. As this diluent solution for diluting a blood sample, an aspect using a diluent solution which does not contain a normal component homeostatically present in blood is preferable. The phrase "does not contain" in the present specification means that a diluent solution "substantially does not contain" a normal component. The phrase "substantially does not contain" means that a diluent solution does not contain a homeostatic substance used for obtaining a dilution factor at all, or means a case in which, even in a case where a diluent solution contains a homeostatic substance, an ultra-small amount of concentration is contained to the extent that does not affect measurement of a homeostatic substance in a diluent solution after diluting a blood sample. In a case where sodium ions or chloride ions are used as a normal component homeostatically present in blood, an aspect in which a diluent solution which substantially does not contain sodium ions or chloride ions is used as a diluent solution is preferable.

In the present invention, after a blood sample collected by a patient or subject to be tested is diluted, it is possible to transport the sample to a medical institution or a test institution so that a concentration of a target component is analyzed. There is a possibility that a long period of time is taken from blood collection to analysis, and therefore during this time, it is preferable to prevent decomposition or denaturation of a target component of blood in a diluent solution. A pH of blood is generally maintained constant at a pH of about 7.30 to 7.40 for healthy subjects. Accordingly, in order to prevent decomposition or denaturation of a target component, a diluent solution is preferably a buffer solution having a buffering action within a pH range of pH 6.5 to pH 8.0, preferably pH 7.0 to pH 7.5, and further preferably pH 7.3 to pH 7.4, and the diluent solution is preferably a buffer solution containing a buffering component for suppressing variation in pH.

As the type of the buffer solution, there are an acetate buffer solution (Na), a phosphate buffer solution (Na), a citrate buffer solution (Na), a borate buffer solution (Na), a tartrate buffer solution (Na), a Tris (tris(hydroxymethyl) aminoethane) buffer solution (Cl), a HEPES ([2-[4-(2-hydroxyethyl)-1-piperazinyl]ethanesulfonic acid]) buffer solution, a phosphate buffered saline (Na), and the like. Among these, as a buffer solution around pH 7.0 to pH 8.0, a phosphate buffer solution, a Tris buffer solution, and a HEPES buffer solution are representative. However, the phosphate buffer solution contains a sodium salt of phosphoric acid, the Tris buffer solution has a dissociation pKa of 8.08, and thus is usually used in combination with hydrochloric acid for imparting buffering ability around pH 7.0 to pH 8.0, and a dissociation pKa of sulfonic acid of HEPES is 7.55, but in order to adjust buffer solution at constant ionic strength, a HEPES mixture of sodium oxide and sodium chloride is used. Therefore, these solutions are useful as a buffer solution having an action of maintaining pH constant, but contain sodium ions or chloride ions which are substances preferably used as an external standard substance in the present invention, and thus, application thereof to the present invention is not preferable.

As the diluent solution included in the kit of the present invention, it is preferable to use a buffer solution which does not contain sodium ions or chloride ions. The diluent solution used in the present invention is preferably a diluent solution including at least an amino alcohol compound selected from the group consisting of 2-amino-2-methyl-1- propanol (AMP), 2-ethylaminoethanol, N-methyl-D-glucamine, diethanolamine, and triethanolamine, and a buffering agent selected from the group consisting of 2-[4-(2-hydroxyethyl)-1-piperazinyl]ethanesulfonic acid (pKa=7.55) also called HEPES which is a buffering agent having a pKa around 7.4, N-tris(hydroxymethyl)methyl-2-aminoethanesulfonic acid also called TES (pKa=7.50), 3-morpholinopropanesulfonic acid also called MOPS (pKa=7.20), and N,N-bis(2-hydroxyethyl)-2-aminoethanesulfonic acid also called BES (pKa=7.15), which are Good's buffer solutions (Good's buffers). Among these, a combination of 2-amino-2-methyl-1-propanol (AMP) with HEPES, TES, MOPS, or BES is preferable, and a combination of 2-amino-2-methyl-1-propanol (AMP) with HEPES is most preferable.

For preparing the buffer solution described above, an amino alcohol may be mixed with the Good's buffer solutions at a concentration ratio of 1:2 to 2:1, preferably 1:1.5 to 1.5:1, and more preferably 1:1. A concentration of the buffer solution is not limited, but a concentration of the amino alcohol or the Good's buffer solution is 0.1 to 1000 mmol/L, preferably 1 to 500 mmol/L, and more preferably 10 to 100 mmol/L.

A chelating agent, a surfactant, an antibacterial agent, a preservative, a coenzyme, a saccharide, and the like may be contained in the buffer solution in order to keep a target component to be analyzed stable. Examples of chelating agents include a salt of ethylenediaminetetraacetic acid (EDTA), citrate, oxalate, and the like. Examples of the surfactant include a cationic surfactant, an anionic surfactant, an amphoteric surfactant, and a nonionic surfactant. Examples of the preservative include sodium azide, antibiotics, and the like. Examples of the coenzyme include pyridoxal phosphate, magnesium, zinc, and the like. Examples of the saccharide of a red blood cell-stabilizing agent include mannitol, dextrose, oligosaccharide, and the like. Particularly, by adding the antibiotics, it is possible to suppress the growth of bacteria which are partially mixed from the surface of the finger at the time of collecting blood from the finger, and stabilize the decomposition of biological components by bacteria.

It is important that these buffer solutions do not contain a normal component homeostatically present in blood and an internal standard substance, and do not interfere with a measuring system. In addition, it is preferable that components diluted with these buffer solutions are not interfered even by various measuring methods using the biochemical/automated immunoassay analyzer, that blood cells are not hemolyzed, and that biological components can be stored stably even at 37° C.

In a case where whole blood is used for a blood sample, blood cell components in diluted blood is required to be separated through a filter, and by setting osmotic pressure of the buffer solution equivalent to (285 mOsm/kg (mOsm/kg is an osmotic pressure that 1 kg of water of the solution has, and indicates millimoles of ions)) or higher than that of the blood, it is possible to prevent hemolysis of blood cells. The osmotic pressure can be adjusted to be isotonic by measurement of a target component; salts, saccharides, or buffering agents, which do not affect measurement of a normal component homeostatically present in blood; and the like.

[Volume of Diluent Solution and Dilution Factor]

In a case of testing a specific organ or a specific disease such as liver function, renal function, metabolism, and the like as a blood test, analysis of a plurality of target components to be measured is generally performed at the same time in order to perform a prediction and the like of a state of the organ, a lifestyle habit, and the like by obtaining information of the plurality of target components to be measured which are specific to the organ or the disease. For example, in order to test the state of a liver, generally, a concentration of various substances in the blood such as ALT (alanine transaminase), AST (aspartate aminotransferase), γ-GTP (γ-glutamyl transpeptidase), ALP (alkaline phosphatase), total bilirubin, total protein, and albumins is measured. As above, in order to measure the plurality of target components from one blood sample, a certain volume of diluted blood is required in a case of considering a possibility of measuring again. Accordingly, regarding a diluent solution for diluting the collected blood, it is important that a certain volume thereof is secured. A volume of the diluent solution in the kit is preferably 4 times or more a volume of blood plasma (that is, a dilution factor is 5 times or more a volume of blood plasma), is more preferably 10 times or more, and is even more preferably 14 times or more. For example, in a case where a volume of blood collected is 50 μL, and in a case where a rate of an amount of blood plasma in the volume of blood collected is 0.55, a volume of blood plasma can be calculated as 27.5 μL, and in a case where the diluent solution is 360 μL, a dilution factor is 14. Assuming a volume of blood plasma and a volume of diluent solution, which are obtained by calculation from a dilution factor in a case of using blood plasma as a reference, are R and S, respectively, a dilution factor can be estimated with the blood sample as a reference by obtaining (R+0.55×S)/R. A volume of diluent solution used for the blood analysis is preferably 2.7 times or more, more preferably 6.0 times or more, and even more preferably 8.2 times or more with respect to a volume of a blood sample.

[Separation Instrument for Separating and Recovering Blood Plasma from Dilution of Blood Sample]

There is a possibility that a blood sample collected for the blood analysis method of the embodiment of the present invention is left alone for a long period of time in a diluted state before performing the analysis. During the time, for example, in a case where red blood cells are hemolyzed, substances, enzymes, and the like which are present in the blood cells are eluted into the blood plasma or blood serum, and therefore a test result is affected thereby. Furthermore, there is a possibility that an absorption amount of the eluted hemoglobin affects a case of measuring an amount of a target component to be analyzed with light information such as the optical absorption of the target component to be analyzed, and the like. The present invention makes enables measurement of a target substance with high accuracies by correction even at the time of hemolysis, but in order to reduce the cause of errors, it is preferable to curb a degree of hemolysis as small as possible. For this reason, an aspect in which a separation instrument for separating and recovering blood plasma from a dilution of a blood sample is contained in a blood test kit is preferable. A preferred example of the separation instrument is a separation membrane. It is possible to use the separation membrane such that blood cells are separated and blood plasma components are recovered by applying pressure to the diluent solution of a blood sample, trapping the blood cell components with the separation membrane, and allowing the blood plasma components to pass through the separation membrane. In this case, it is preferable that an anticoagulant is used. In addition, in order to ensure the accuracy of measurement, it is preferable that backflow of the blood plasma passed through the separation membrane to the blood cells side does not occur. Therefore, specifically, the kit can include a backflow prevention means described in JP2003-270239A as a constituent component.

[2] Blood Test Kit

The blood analysis method of the embodiment of the present invention can be performed using a blood test kit preferably including a diluent solution for diluting a blood sample, separation means for recovering blood plasma components from the diluted blood sample, and a container for storing the blood plasma components recovered from the diluted blood sample.

The blood test kit more preferably includes a collection instrument for collecting blood, a first storing instrument for storing a diluent solution, a separation instrument for separating and recovering blood plasma from a diluted blood sample, a holding instrument for holding the separation instrument, and a second storing instrument for storing the blood plasma recovered from the diluted blood sample.

In addition to the above-described instruments, the blood test kit further preferably includes a sealing instrument for keeping the stored blood plasma within the second storing instrument.

As the example of the blood test kit of the present invention, the kit can include a diluent solution for diluting components in a blood sample, a first storing instrument in which the diluent solution is stored, a separation instrument for separating and recovering blood plasma from the blood sample diluted with the diluent solution, a holding instrument for holding the separation instrument, a second storing instrument for storing the recovered blood plasma, a sealing instrument for keeping the stored blood plasma in the second storing instrument, a needle or a lancet for pricking the skin to allow blood to flow out of the skin, a strip of bandage or a sterile swab to be put on the wound (for example, nonwoven fabrics impregnated with isopropanol (70% isopropanol and the like), ethanol, or the like), an instruction manual, and the like. As the separation instrument for recovering blood plasma components from the diluted blood sample, an aspect of the separation membrane is preferable, and a filter having fine pores capable of separating blood cell components is more preferable.

Regarding the first storing instrument and the second storing instrument, one instrument may be used as both the first storing instrument and the second storing instrument, or an embodiment in which instruments are provided separately may be used. The first storing instrument and the second storing instrument are preferably made of a transparent material such that a patient or a measurer who performs measurement of a dilution factor and analysis of a target component to be analyzed can check a diluent solution in the storing instrument, by which the blood is diluted.

As the holding instrument for holding the separation instrument, an aspect of a gasket is preferable. In addition, as the sealing instrument, in a case where the storing instrument is an instrument having a tubular shape, and the like, it is possible to use a cap capable of being used as a lid for the opening, a lid having a helical groove, a rubber closure, and the like.

With the above configuration, by imparting the function of separating blood plasma from blood cells to the container in which the blood is mixed with the diluent solution immediately after diluting the blood with the diluent solution, it is possible to eliminate the influence on the stability of the blood components and the variation of the components due to hemolysis from blood cells, and to impart the stability to the specimen after blood collection.

The blood analysis method of the embodiment of the present invention is capable of realizing a method in which a target component to be analyzed can be analyzed at high measurement accuracy even with a volume of blood collection of 100 μL or less. The blood test kit for blood analysis preferably includes an instruction manual in which information that measurement can be accurately performed even with a small volume of blood collection of 100 μL or less, and the like is described for a patient.

[Specific Example of Blood Test Kit]

Figure 1:
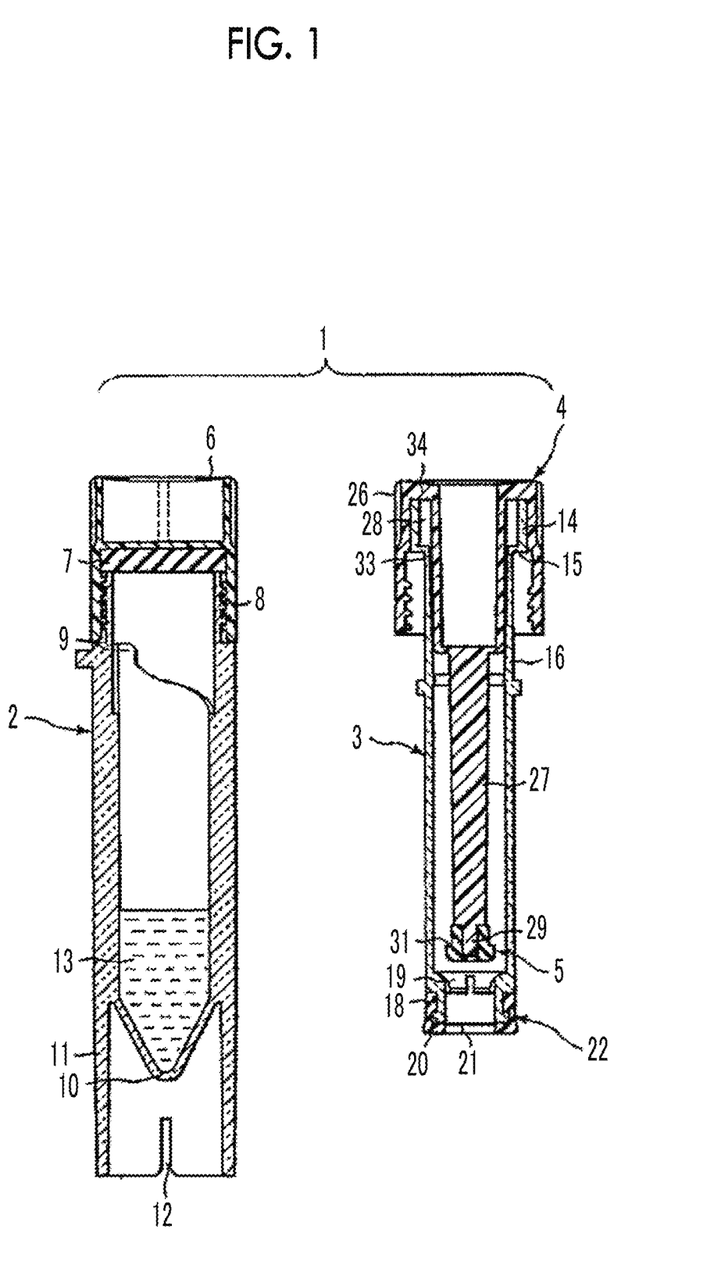
FIG. 1 is a cross sectional diagram of a blood test kit according to an embodiment of the present invention.

In one preferred embodiment, the blood test kit for blood analysis includes, in addition to the capillary, the diluent solution, the first storing instrument in which the diluent solution is stored (which also may be a storing instrument for storing a dilution of a blood sample), the separation instrument for separating and recovering blood plasma from a blood sample diluted with the diluent solution, the holding instrument for holding the separation instrument, the second storing instrument for storing the recovered blood plasma, and the sealing instrument for keeping the stored blood plasma in the second storing instrument. As specific examples of the instruments, it is possible to use instruments described in FIG. 1 to FIG. 13 of JP3597827B. FIG. 1 of JP3597827B is incorporated as FIG. 1 of the present application.

A blood separation instrument 1 includes a blood collection container 2 (storing instrument in which a diluent solution is stored, which may be referred to as the first storing instrument in some cases. This is a storing instrument for storing a dilution of a blood sample), a tubular body 3 capable of being to fit into the blood collection container 2 so as to be inserted (second storing instrument for storing recovered blood plasma), a cap piston 4 capable of being capped on the tubular body 3, and a sealing lid 5 (sealing instrument) provided at a lower end of the cap piston 4. Before use, an upper end opening portion of the blood collection container 2 is sealed by a cap 6 via a packing 7, as shown in FIG. 1. The storing instrument for storing a diluted blood sample of the present invention corresponds to a combination of the blood collection container 2 and the tubular body 3 in the configuration of FIG. 1. That is, the storing instrument for storing a diluted blood sample may be one or a combination of two or more thereof.

The blood collection container 2 is made of a transparent material and has a cylindrical shape. At the upper end portion thereof, a screw portion 8 is formed on the outer surface, and a locking portion 9 is protruded toward the inner surface. In addition, at a lower end portion of the blood collection container 2, a bottom portion 10 having an inverted conical shape is formed, and a cylindrical leg portion 11 is formed around the bottom portion 10. The leg portion 11 has the same outer diameter as a sample cup used at the time of an analytical test of blood, and at positions opposite to the lower end thereof, slit grooves 12 are preferably formed in a vertical direction, respectively. Furthermore, a predetermined volume, for example, 500 mm$^3$ of a diluent solution 13 may be put in the blood collection container 2 in advance, as shown in FIG. 1.

The tubular body 3 is made of a transparent material and has a cylindrical shape, and at an upper end portion thereof, an expanded diameter section 14 is formed. The expanded diameter section 14 is connected to a main body portion 16 via a thin portion 15. A reduced diameter section 18 is formed at the lower end portion of the tubular body 3, and a protruded locking portion 19 is formed on the inner surface of the reduced diameter section 18. Furthermore, at a lower end portion of the reduced diameter section 18, an outer flange portion 20 (holding instrument) is formed, a lower end opening portion of the outer flange portion 20 is covered with a filtration membrane 21 (separation instrument), and the filtration membrane 21 allows blood plasma in the blood to pass through and prevents passage of the blood cells.

A cover 22 made of silicone rubber is attached to the outer periphery of the reduced diameter section 18 (FIG. 1).

The cap piston 4 is constituted by a substantially cylindrical knob portion 26 and a mandrel portion 27 concentric with the knob portion 26 and extending downward. At an inner upper end portion of the knob portion 26, a cylindrical space 28 into which the expanded diameter section 14 of the tubular body 3 is capable of being fitted to be inserted is formed, and the knob portion is threaded in a lower portion into which a screw can screw. The mandrel portion 27 has a lower end portion 29 formed in a pin shape, and the sealing lid 5 is attachably and detachably provided on the lower end portion 29 (refer to FIG. 1). The sealing lid 5 is made of silicone rubber.

Specifically, the operation of separating and recovering blood plasma from a dilution of a blood sample is performed as below. The collected blood is added to the blood collection container 2 storing the diluent solution, and then the blood and the diluent solution are thoroughly shaken to be mixed while noting that bubbles are not generated by holding an upper portion of the blood collection container 2. Next, the tubular body 3 holding the filtration membrane 21 (for preventing solution leakage due to infiltration into a side surface of a cylinder at the time of separating blood plasma from blood cells) is inserted into the blood collection container 2 such that the filtration membrane faces downward, and the filtration membrane is slowly pushed into the bottom of the blood collection container 2 at a constant speed. At this time, the blood plasma passes through the filtration membrane of the tubular body 3 and then floats on the upper portion, and the blood cells remain on the lower portion of the blood collection container 2. Thereafter, the cap piston 4 is slowly pushed into the tubular body 3, by which mixing of the blood plasma with the blood cells due to backflow is prevented by the sealing lid 5.

A method for separating blood by the instruments described above is described in detail in paragraphs 0023 to 0026 and FIG. 12 and FIG. 13 of JP3597827B, the contents of which are incorporated in the present specification.

The number of various components contained in the blood test kit for blood analysis of the embodiment of the present invention is not particularly limited, and each component may be one, or there may be a plurality of, for example, 2 or more thereof.

The material of the member included in the blood test kit for blood analysis of the embodiment of the present invention is preferably a synthetic resin from the viewpoints of difficulty in breakage, sanitation, price, and the like. Examples thereof include polyethylene, polypropylene, polyvinyl chloride, polyvinylidene chloride, polystyrene, polyvinyl acetate, polyurethane, polyethylene terephthalate, polylactic acid, acrylonitrile butadiene styrene resin (ABS resin), acrylonitrile styrene resin (AS resin), acrylic resin (PMMA), polycarbonate, silicone resin, and the like.

The blood test kit for blood analysis of the embodiment of the present invention can provide all members in an aspect in which the members are stored in the storing container. A material of the member used for the blood test kit for blood analysis of the embodiment of the present invention may be plastic, glass, or rubber.

[3] Others

The present invention provides a blood analysis method using the blood test kit configured as described in [1] and [2] of the present specification. The blood analysis method includes an aspect which is a medical practice (practice performed by a doctor) for humans and an aspect which is not a medical practice for humans (for example, an aspect in which a person who performs blood collection is a patient himself and an analyzer is a person other than a doctor, an aspect for non-human animals, and the like). The blood analysis method of the present invention may be performed by the self-blood collection in which a subject to be tested collects blood by himself, or may be performed by the general blood collection in which a qualified person such as a doctor collects blood using a syringe. As a preferred embodiment, a patient pricks the fingertip and the like by himself using an instrument equipped with a small blade such as a lancet, and then collects blood flowing out of the skin.

In the present invention, a biological specimen which is a target of the blood analysis method of the embodiment of the present invention is blood, and the blood is a concept of including serum or blood plasma. The origin of blood is not limited to humans, and may be mammals, birds, fish, and the like which are animals other than humans (non-human animals). Examples of the animals other than humans include horses, cows, pigs, sheep, goats, dogs, cats, mice, bears, pandas, and the like. The origin of a biological specimen is preferably humans.

In a case of performing the blood analysis of the embodiment of the present invention, the target component to be analyzed is not limited and any substance contained in blood is a target. Examples thereof include biochemical test items in blood used for clinical diagnosis, markers of various diseases such as tumor markers and hepatitis markers, and the like, and include proteins, saccharides, lipids, low molecular weight compounds, and the like. In addition, not only a concentration of a substance is measured, but also an activity of a substance having an activity such as an enzyme is targeted. Analysis of each target component can be carried out by a known method.

EXAMPLES

Hereinafter, examples of the present invention will be explained.

(Preparation of Diluent Solution)

Diluent Solution-1 was prepared with the following composition. As osmotic pressure, a value measured by using OSMOATAT OM-6040 (manufactured by ARKRAY, Inc.) is shown. A unit of the osmotic pressure is an osmotic pressure that 1 kg of water of a solution has, and indicates millimoles of ions.

| | |
|---|---|
| HEPES | 50 mmol/L |
| 2-amino-2-methyl-1-propanol (AMP) | 50 mmol/L |
| D-Mannitol | 284 mmol/L |
| Lithium chloride | 1 mmol/L |
| EDTA-2K | 0.8 mmol/L |
| Pyridoxal phosphate (PALP) | 0.05 mmol/L |
| Thiabendazole | 0.0001% by mass |
| Amikacin sulfate | 0.0003% by mass |
| Kanamycin sulfate | 0.0005% by mass |
| Meropenem trihydrate | 0.0005% by mass |
| Osmotic pressure | 355 mOsm/kg |
| pH 7.4 | |

(Measurement of Concentration of Sodium)

The measurement of a concentration of sodium in the diluent solution prepared above was carried out by the enzyme activity method utilizing that β-galactosidase is activated by sodium, which is that each concentration of sodium in the diluent solution and β-galactosidase activity are in a proportional relationship. Specifically, after diluting Diluent Solution-1 five times, which was filtered as above with purified water not containing sodium ions, 3 µL was weighed, 52 µL of a first reagent prepared as described below was added thereto, and then heated at 37° C. for 5 minutes. 26 µL of a second reagent prepared as described below was added thereto, and the change in absorbance was obtained by measuring an absorbance during 1 minute at a main wavelength of 410 nm and a complementary wavelength of 658 nm by using JCA-BM6050-type automatic biochemistry analyzer (manufactured by JEOL Ltd.). The concentration of sodium was measured from a calibration curve prepared in advance.

(Preparation of Reagent for Measuring Sodium)

A reagent for measuring sodium having the following composition was prepared.

| First reagent | |
|---|---|
| HEPES•LiOH (pH 8.0) | 100 mmol/L |
| D-Mannitol | 60 mmol/L |
| N-acetylcysteine | 30 mmol/L |
| Magnesium sulfate | 1.52 mmol/L |
| β-galactosidase | 1.1 kU/L |
| TRITON X-100 | 0.05% by mass |
| Second reagent | |
| HEPES•LiOH (pH 8.0) | 100 mmol/L |
| o-Nitrophenyl-β-D-galactopyranoside | 15 mmol/L |

(Measurement of Concentration of Total Protein in Mixed Solution of Blood Plasma and Diluent Solution)

Measurement using the biuret method as the measurement principle was performed. Biuret reagent: 3.0 mmol/L, copper sulfate 400 µl, potassium sodium tartrate 21.3 mmol/L, and NaOH 0.75 mol/L were prepared and mixed with the diluted blood plasma. After mixing, the solution was allowed to stand at 37° C. for 10 minutes, it was waited until a complex exhibiting a blue-violet color of 540 to 560 nm due to protein and copper ions in the blood plasma is formed under the alkaline condition, and an absorbance was measured at 545 nm. The concentration of total protein in the mixed solution of blood plasma and a diluent solution was quantitatively determined using a calibration curve obtained from the absorbance of a standard solution.

1. Preparation of Sample

Using DEMECAL Kit (manufactured by Leisure, Inc.), the diluent solution prepared above and blood collected so that a dilution factor became 8.8 times were weighed and mixed. A sample obtained by quickly pressing a cylinder, which was used at the separation operation performed when preparing diluted blood plasma, and a sample obtained by slowly pressing the cylinder for 5 seconds or more, were created. Therefore, a specimen in which hemolysis was forcibly caused and a specimen in which hemolysis was extremely curbed were prepared. By mixing the two samples thus prepared at various ratios, five types of samples having different degrees of hemolysis were created. Measurement of a degree of hemolysis was measured on the five types of samples by quantitatively determining a concentration (mg/dL) of hemoglobin using a hemoglobin determination reagent with the 7180 Hitachi automatic analyzer. This concentration (mg/dL) of hemoglobin was used as a degree of hemolysis. Evaluation using an automatic analyzer and a measurement reagent was performed according to attached documents and instruction manual.

Figure 2:
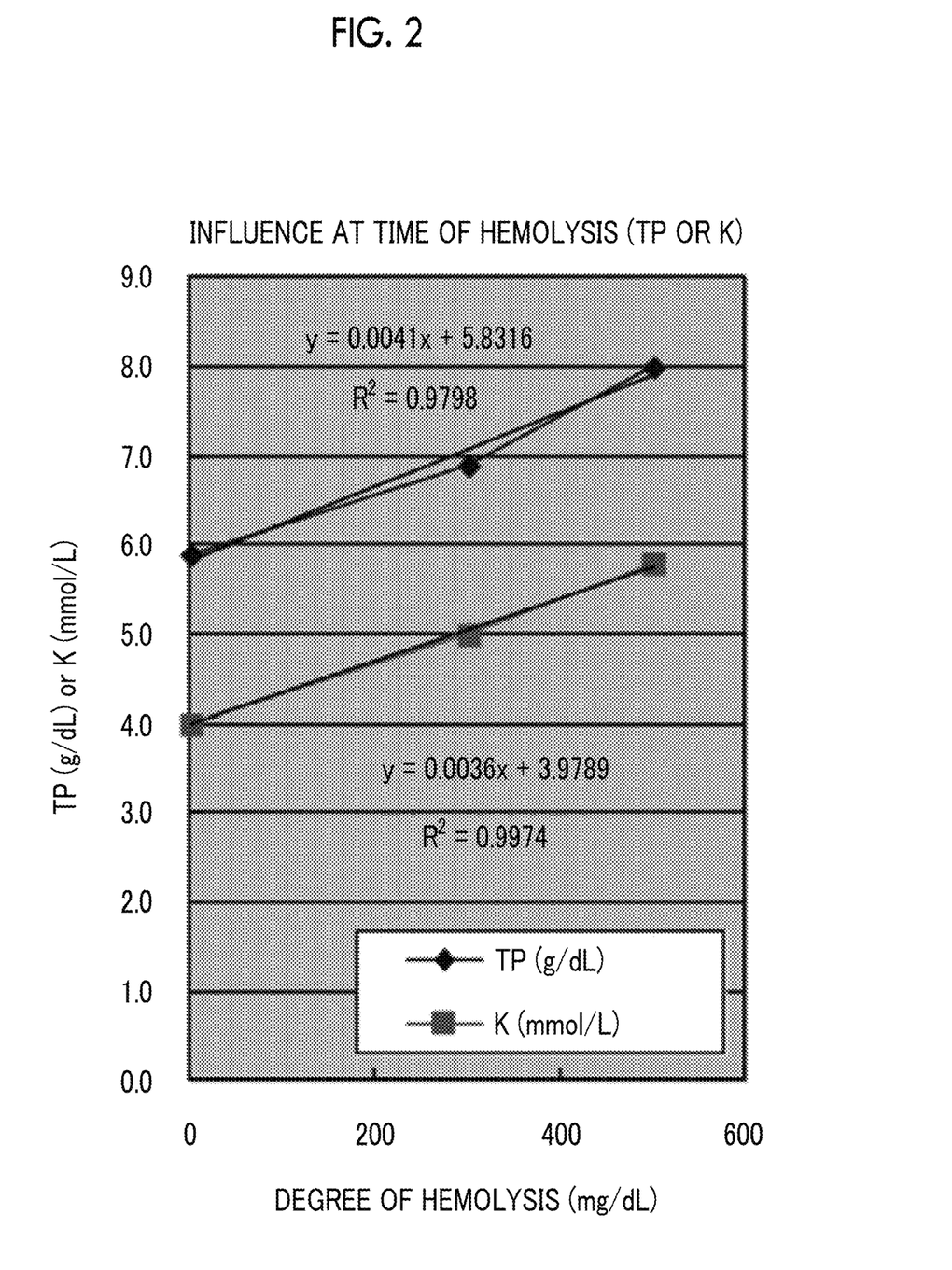
FIG. 2 is a graph showing a relationship between a degree of hemolysis, and a concentration of total protein and a concentration of potassium in blood plasma.
Figure 3:
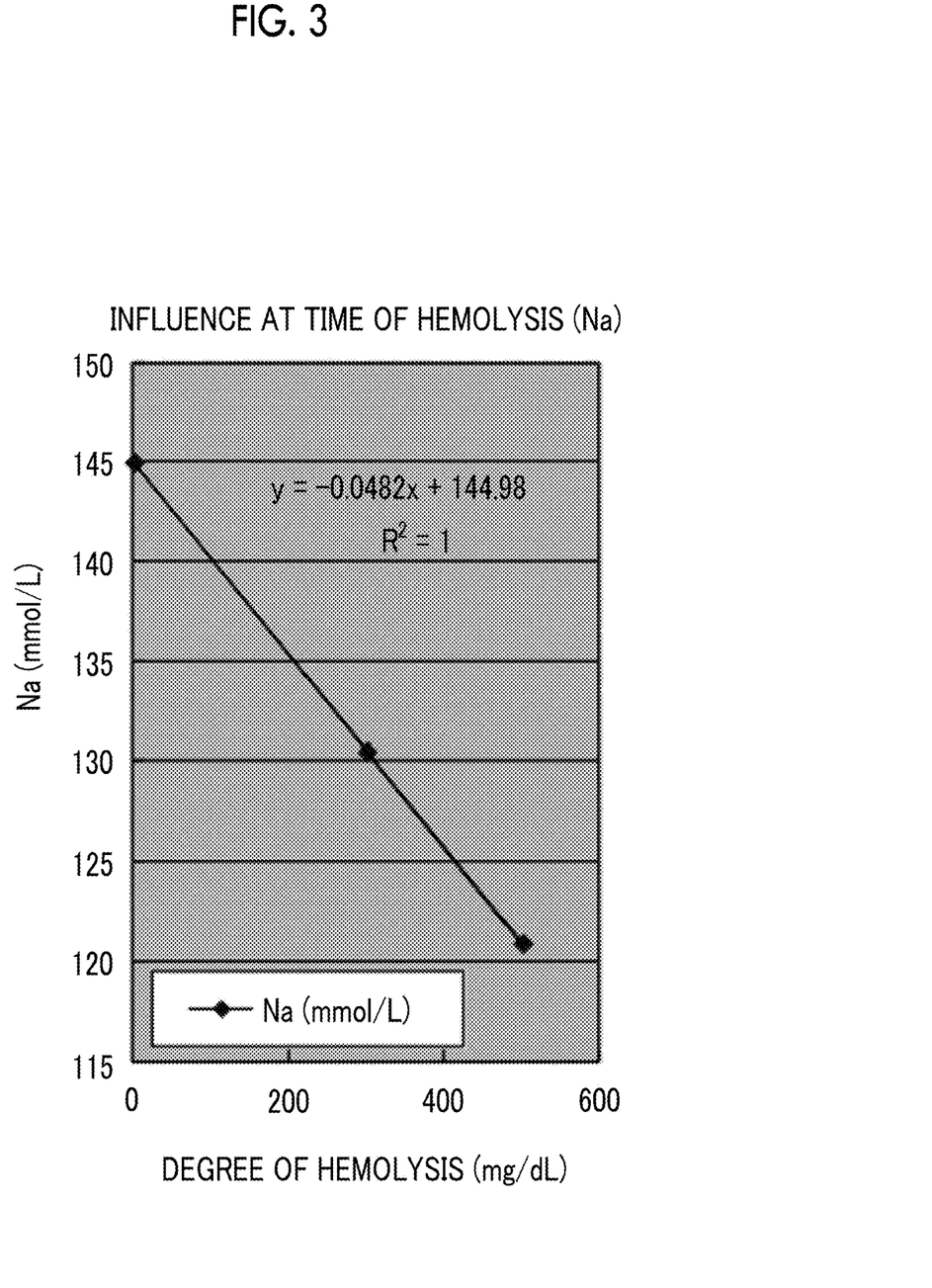
FIG. 3 is a graph showing a relationship between a degree of hemolysis and a concentration of sodium in blood plasma.

2. Variation in Accuracies of Normal Component Due to Influence of Degree of Hemolysis of Normal Component Using total protein (TP), sodium ion (Na), and potassium ion (K) as normal components present in blood, an Na concentration, a K concentration, and a TP concentration, all of which were not diluted, of the five types of samples having different degrees of hemolysis prepared as described were obtained using a dilution factor of 8.8 times. FIG. 2 and FIG. 3 shows graphs which plot a degree of hemolysis of hemoglobin on a lateral axis, and each of concentrations on a vertical axis. As described above, it can be understood that each of content concentration value varies according to a degree of hemolysis. In a case where a concentration of a normal component in the mixed solution of blood plasma and a diluent solution increases at the time of hemolysis, an apparent dilution factor decreases. Conversely, in a case where the concentration of a normal component decreases, an apparent dilution factor increases.

3. Correction in Case where Total Protein is Normal Component

TP concentrations of the five types of samples having different degrees of hemolysis prepared in 1. were measured using the reagent for measuring TP concentration described above with the 7180 Hitachi automatic analyzer. A TP concentration in blood plasma of each of the samples was calculated using a dilution factor of 8.8. The calculated TP concentration is supposed to be the same value as that of a normal component, but the TP concentration in blood plasma became a high value according to a degree of hemolysis. This reflects results in which the TP concentration in blood plasma increases due to hemolysis. Accordingly, in a case where a dilution factor is obtained as in the following equation using a TP concentration value in blood plasma without hemolysis (a normal value in a case where a measurement value is not calculated), and a measurement value of the TP concentration in the mixed solution of blood plasma and a diluent solution, a measurement value (A) of the TP concentration in the mixed solution of blood plasma and a diluent solution increases according to a degree of hemolysis. Therefore, an apparent dilution factor became low as shown in (Table 1).

Apparent dilution factor=value of TP concentration in blood plasma without hemolysis/measurement value ($A$) of TP concentration      Equation 10:

A unit of a value of TP concentration in blood plasma without hemolysis and a measurement value (A) of TP concentration is g/dL.

As shown below, a concentration of total protein in blood plasma were corrected using an amount of total protein increased due to hemolysis. This correction was calculated from the following equation using a degree of hemolysis (a concentration (mg/dL) of hemoglobin) and measurement concentration (U) of hemoglobin in a blood plasma diluent solution, which were obtained in 2.

Corrected TP concentration=(value of TP concentration in blood plasma without hemolysis)−(measurement concentration ($U$) of hemoglobin)×(dilution factor)×0.0041      Equation 11:

(In Equation 11, 0.0041 represents a slope of a degree of hemolysis and a TP amount)

A unit of the corrected TP concentration is g/dL.

Using the corrected TP concentration and the measurement value (A) of TP concentration, a dilution factor of each of the five samples was calculated by the following method.

corrected dilution factor=corrected TP concentration/
measurement value (A) of TP concentration   Equation 12:

The calculation results of corrected dilution factors are shown in Table 1. It was confirmed that the corrected dilution factors can be made constant by correcting the measured TP concentration in the mixed solution using the relationship between a degree of hemolysis and a TP concentration according to the hemolysis shown in FIG. 2.

4. Correction Results of Total Cholesterol (TC)

Figure 4:
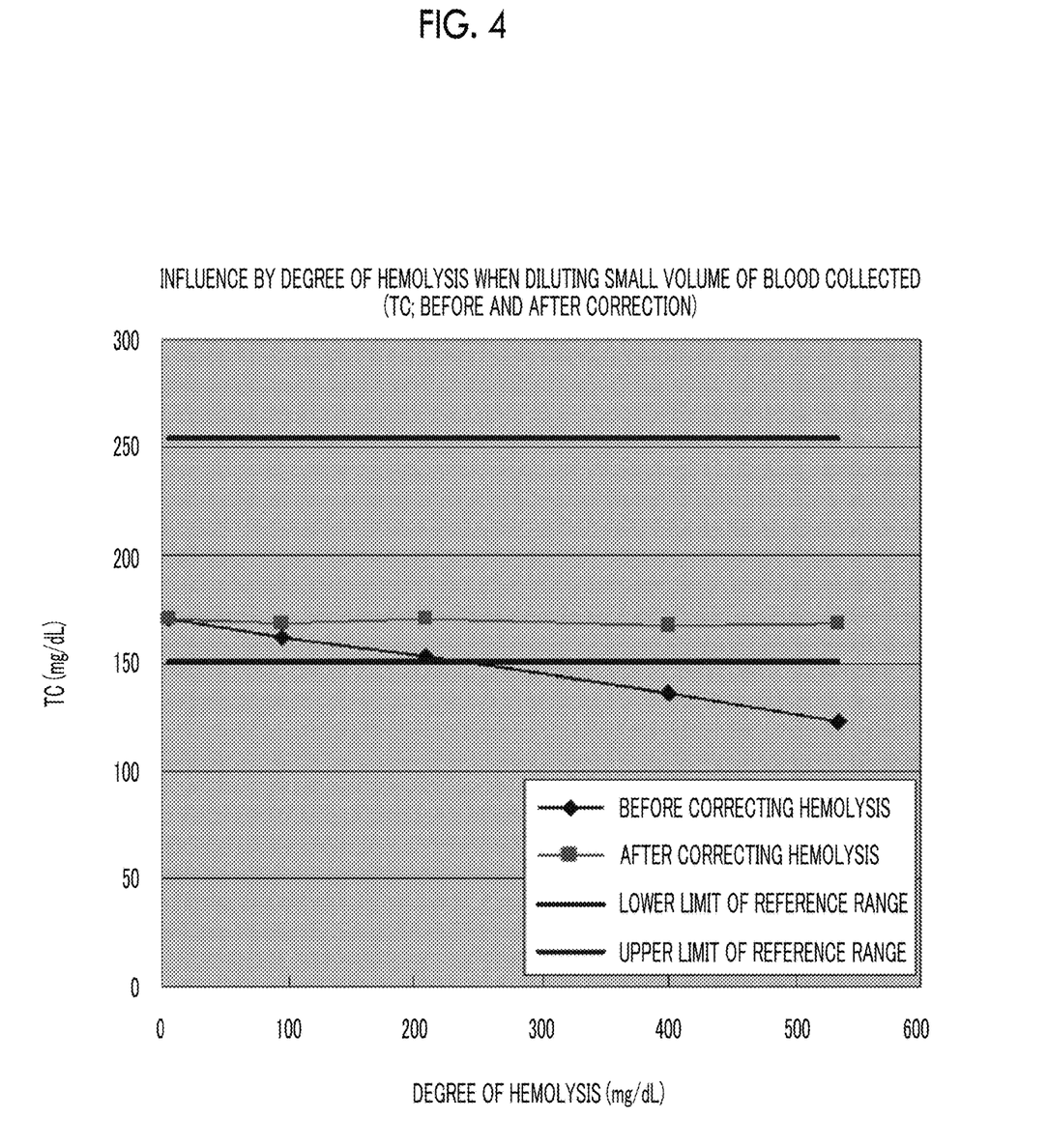
FIG. 4 is a graph showing calculated values of a concentration of total cholesterol in blood plasma, with or without correction with a degree of hemolysis.

Using the five types of samples having different degrees of hemolysis which were used in 1., total cholesterol (TC) as a target component to be analyzed was measured using a reagent for measuring total cholesterol (TC) with the 7180 Hitachi automatic analyzer. In the same manner as in 3., calculation of a concentration of total cholesterol before hemolysis correction was performed by multiplying the value of the apparent dilution factor obtained in 3. by a measurement value. Calculation of a concentration of total cholesterol after hemolysis correction was performed using the corrected dilution factor obtained in 3. The calculated results are shown in Table 1. A measurement value decreases according to a degree of hemolysis in a case where hemolysis correction was not performed, and errors are large and fall below a lower limit of a reference range in a case where a degree of hemolysis is high. However, by correcting a dilution factor by a degree of hemolysis, a result which was not affected by a degree of hemolysis was obtained. FIG. 4 shows a plot of a change in TC concentration with respect to a degree of hemolysis with and without hemolysis correction. It can be understood that a TC concentration does not change irrespective of a degree of hemolysis by performing the correction.

TABLE 1

| Degree of hemolysis | Total protein as normal component | | Corrected dilution factor | Total cholesterol (TC) | |
|---|---|---|---|---|---|
| | Measurement value of TP (g/dL) | Apparent dilution factor | | Before correcting hemolysis | After correcting hemolysis |
| 0 | 5.9 | 8.8 | 8.8 | 170 | 170 |
| 95 | 6.2 | 8.4 | 8.7 | 162 | 167 |
| 210 | 6.8 | 7.7 | 8.8 | 148 | 170 |
| 400 | 7.6 | 6.8 | 8.9 | 132 | 172 |
| 535 | 8.1 | 6.4 | 8.8 | 124 | 170 |

5. Case where Sodium was Used as Normal Component

Measurement of sodium contained in the five types of samples having different degrees of hemolysis which were used in 1. was performed using the reagent for measuring sodium prepared as above with the 7180 Hitachi automatic analyzer. In the same manner as in 3., calculation of a NA concentration before hemolysis correction was performed by multiplying the value of the dilution factor of 8.8 times used in 3. by a measurement value of a NA concentration. The calculated values (measurement values of Na) are shown in Table 2. The calculated Na concentration is supposed to be the same value as that of a normal component, but the Na concentration in blood plasma became a low value according to a degree of hemolysis. This reflects results in which the Na concentration in blood plasma decreases due to hemolysis. Accordingly, in a case where a dilution factor is obtained as in the following equation using a Na concentration value in blood plasma without hemolysis (a normal value in a case where a measurement value is not calculated), and a measurement value of the Na concentration in the mixed solution of blood plasma and a diluent solution, a measurement value (B) of the Na concentration in the mixed solution of blood plasma and a diluent solution decreases according to a degree of hemolysis. Therefore, an apparent dilution factor became larger as shown in Table 2.

Apparent dilution factor=value of Na concentration
in blood plasma without hemolysis/measurement value (B) of Na concentration   Equation 13:

A unit of a value of Na concentration in blood plasma without hemolysis and a measurement value (B) of Na concentration is mmol/L.

As shown below, an amount of Na concentration decreased by hemolysis was used to correct the Na concentration in blood plasma. This correction was calculated from the following equation using a degree of hemolysis (a concentration of hemoglobin) and measurement concentration (U) of hemoglobin in a blood plasma diluent solution, which were obtained in 2.

Corrected Na concentration=(value of Na concentration in blood plasma without hemolysis)+(measurement concentration (U) of hemoglobin)×
(dilution factor)×0.0482   Equation 14:

(In Equation 14, 0.0482 represents a slope of a degree of hemolysis obtained in FIG. 3 and an Na amount)

A unit of the corrected Na concentration is mmol/L.

Using the corrected Na concentration and the measurement value (B) of Na concentration, a dilution factor of each of the five samples was calculated by the following method.

corrected dilution factor=corrected Na concentration/
measurement value (B) of Na concentration   Equation 15:

The calculation results of corrected dilution factors are shown in Table 2. It was confirmed that the corrected dilution factors can be made constant by correcting the measured Na concentration in the mixed solution using the relationship between a degree of hemolysis and an Na concentration according to the hemolysis shown in FIG. 3.

6. Correction Results of Creatinine (CRE)

Figure 5:
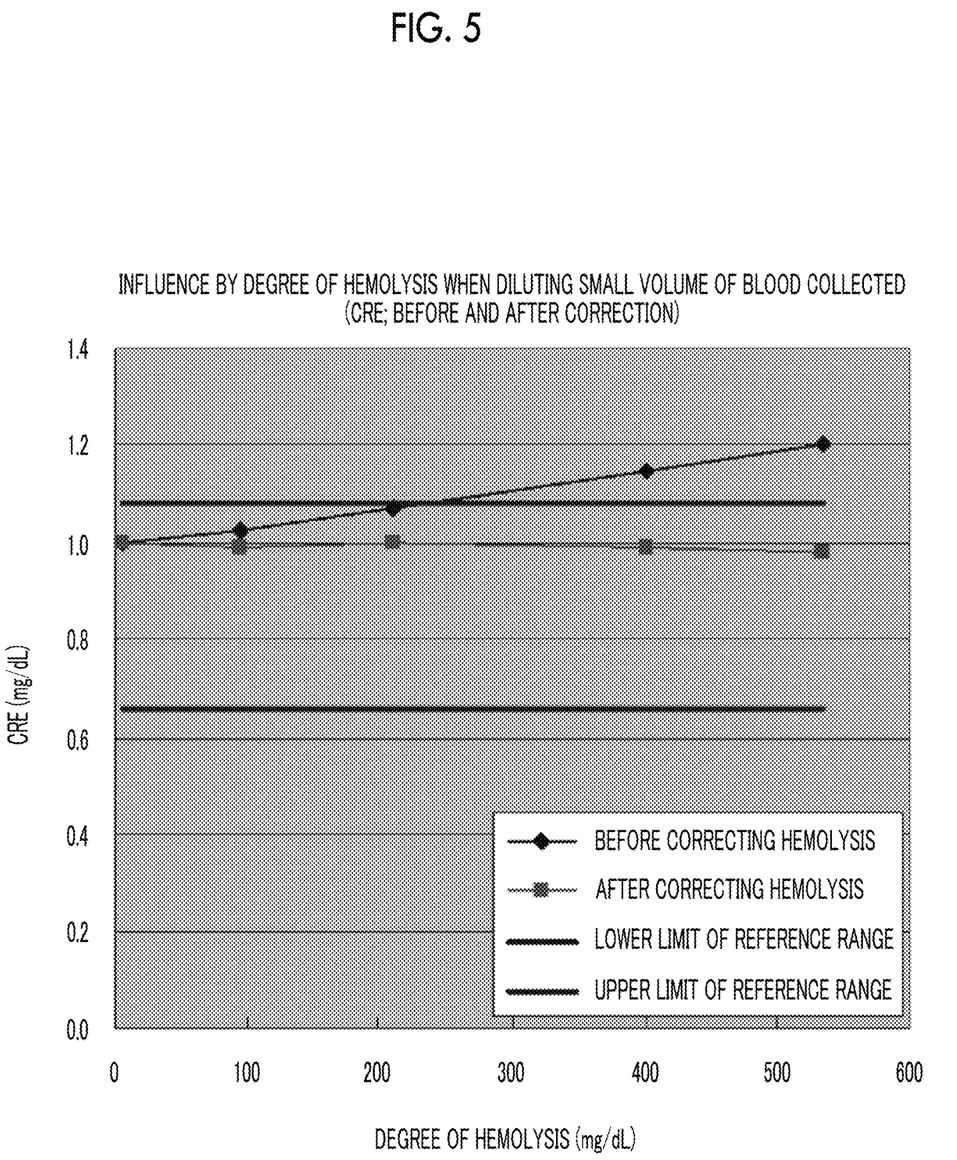
FIG. 5 is a graph showing calculated values of a concentration of creatinine in blood plasma, with or without correction with a degree of hemolysis.

Using the five types of samples having different degrees of hemolysis which were used in 1., creatinine (CRE) as a target component to be analyzed was measured using a reagent for measuring creatinine (CRE) with the 7180 Hitachi automatic analyzer. In the same manner as in 3., calculation of a concentration of CRE before hemolysis correction was performed by multiplying the value of the apparent dilution factor obtained in 5. by a measurement value. Calculation of a concentration of CRE after hemolysis correction was performed using the corrected dilution factor obtained in 5. The calculated results are shown in Table 2. A measurement value increases according to a degree of hemolysis in a case where hemolysis correction was not performed, and errors are large and above an upper limit of a reference range in a case where a degree of hemolysis is high. However, by correcting a dilution factor by a degree of hemolysis, a result which was not affected by a degree of hemolysis was obtained. FIG. 5 shows a plot of a change in CRE concentration with respect to a degree of hemolysis with and without hemolysis correction. It can be understood that a CRE concentration does not change irrespective of a degree of hemolysis by performing the correction.

TABLE 2

| Na as normal component | | | Corrected dilution factor | CRE | |
|---|---|---|---|---|---|
| Degree of hemolysis | Measurement value of Na (mmol/L) | Apparent dilution factor | | Before correcting hemolysis | After correcting hemolysis |
| 0 | 145 | 8.8 | 8.8 | 1.0 | 1.0 |
| 95 | 139 | 9.2 | 8.7 | 1.0 | 1.0 |
| 210 | 136 | 9.4 | 8.9 | 1.1 | 1.0 |
| 400 | 124 | 10.3 | 8.7 | 1.2 | 1.0 |
| 535 | 119 | 10.7 | 8.8 | 1.2 | 1.0 |

EXPLANATION OF REFERENCES

1: blood separation instrument
2: blood collection container
3: tubular body
4: cap piston
5: sealing lid
6: cap
7: packing
8: screw portion
9: locking portion
10: bottom portion
11: leg portion
12: slit groove
13: diluent solution
14: expanded diameter section
15: thin portion
16: main body portion
18: reduced diameter section
19: protruded locking portion
20: outer flange portion
21: filtration membrane
22: cover
26: knob portion
27: mandrel portion
28: space
29: lower end portion
31: level difference portion
33: upper end portion
34: top portion

What is claimed is:

1. A blood analysis method for measuring a concentration of a target component to be analyzed, the blood analysis method comprising:
a step of diluting a collected blood sample with an aqueous diluent solution;
a step of determining a dilution factor by comparing a normal value of a first normal component which is homeostatically present in blood with a measured concentration value of the first normal component in the blood sample diluted with the diluent solution, wherein the normal value is an average homeostatic concentration value of the first normal component in blood plasma; and
a step of analyzing the concentration of the target component to be analyzed in the blood sample,
wherein the diluent solution does not contain the first normal component which is homeostatically present in blood as a component and the method performs measuring an amount of hemolysis in the blood sample,
determining a correction factor based on a predetermined relationship between the amount of hemolysis in the blood sample and a variation in detected concentration of the first normal component in the blood plasma caused by hemolysis,
correcting the dilution factor according to the correction factor, and
analyzing the concentration of the target component to be analyzed using the corrected dilution factor,
wherein the first normal component is one or more of sodium ions, potassium ions, and total proteins.

2. The blood analysis method according to claim 1, which is performed by using a blood test kit,
wherein the blood test kit includes
the diluent solution for diluting the blood sample,
a separating membrane for recovering a blood plasma component from the diluted blood sample; and
a container for storing the blood plasma component recovered from the diluted blood sample.

3. The blood analysis method according to claim 2,
wherein the diluent solution contains a second normal component not present in blood,
the second normal component not present in blood is one or more of glycerol 3-phosphate, an alkali metal, or an alkaline earth metal,
another dilution factor is evaluated by comparing a concentration value of the second normal component not present in blood in the diluent solution with the concentration value of the first normal component which is homeostatically present in blood in the blood sample diluted with the diluent solution, and
the concentration of the target component to be analyzed in the blood sample is evaluated using the corrected dilution factor.

4. The blood analysis method according to claim 2,
wherein the blood plasma component is recovered from the diluted blood sample by using the blood test kit,
a dilution factor of the diluted blood sample is determined using the first normal component which is homeostatically present in the recovered blood plasma component, and
the concentration of the target component to be analyzed in the blood sample is analyzed.

5. The blood analysis method according to claim 2,
wherein the diluent solution contains a second normal component not present in blood,
the second normal component not present in blood is one or more of glycerol 3-phosphate, an alkali metal, or an alkaline earth metal, and
another dilution factor of the diluted blood sample is determined using the second normal component not present in blood, the concentration of the target component to be analyzed in the blood sample is analyzed using the corrected dilution factor.

6. The blood analysis method according to claim 3, wherein the alkali metal is lithium, rubidium, cesium, or francium, and
the alkaline earth metal is strontium, barium, or radium.

7. The blood analysis method according to claim 5, wherein the alkali metal is lithium, rubidium, cesium, or francium, and
the alkaline earth metal is strontium, barium, or radium.

* * * * *